United States Patent [19]

Collen

[11] 4,180,437

[45] Dec. 25, 1979

[54] PURIFICATION OF ANTISERUM FOR THROMBOSIS TEST

[75] Inventor: Désiré J. Collen, Winksele, Belgium

[73] Assignee: Leuven Research & Development V.Z.W., Leuven, Belgium

[21] Appl. No.: 773,308

[22] Filed: Mar. 1, 1977

[30] Foreign Application Priority Data

Mar. 8, 1976 [NL] Netherlands .......................... 7602422

[51] Int. Cl.$^2$ ...................... C07G 7/00; G01N 31/00; G01N 31/14
[52] U.S. Cl. .................................... 435/7; 23/230 B; 424/12; 435/180; 435/803; 435/13
[58] Field of Search .................. 195/103.5 A, 99, 101, 195/63; 424/12; 23/230 B

[56] References Cited

U.S. PATENT DOCUMENTS 3,912,805 10/1975 Cayzer et al. ................ 195/103.5 A

OTHER PUBLICATIONS

Collen, Thrombosis Research, vol. 5, pp. 777–779, 1974.
Collen et al., Thrombosis Research, vol. 7, pp. 235–238, 1975.

Primary Examiner—David M. Naff
Attorney, Agent, or Firm—Lewis H. Eslinger

[57] ABSTRACT

Antiserum which has been generated against an enzyme-inhibitor-complex is purified by immunoprecipitating a freshly generated antiserum with fresh human bloodplasma to form a precipitate and a fluid, and subjecting the fluid to chromatographic separation over an insolubilized enzyme-inhibitor complex against which the antiserum has been generated. A reagent for immunochemical assay is prepared by contacting the purified antiserum with red bloodcells or synthetic resin particles to obtain on the surface of the red bloodcells or synthetic resin particles antibodies from the antiserum. In a diagnosis test, blood plasma is contacted with the purified antiserum and with red bloodcells or synthetic resin particles which bear the enzyme-inhibitor complex used to prepare the antiserum, and whether or not agglutination occurs is ascertained. In an alternative diagnosis test, blood plasma is contacted with red bloodcells or synthetic resin particles having on their surface antibodies from the antiserum, and whether or not agglutination occurs is ascertained.

14 Claims, No Drawings

PURIFICATION OF ANTISERUM FOR THROMBOSIS TEST

The invention relates, in general, to a thrombosis-test to be carried out clinically and, more particularly, to the purification of an antiserum to be used therein.

In U.S. Pat. application Ser. No. 723,187, filed Sept. 13, 1976, now abandoned, a description is given of a method with which, in a relatively simple manner, a possible activation of the blood-coagulation or fibrinolytic system in bloodplasma and thus also the possibility of intravascal blood-coagulation and/or hyperfibrinolysis can be determined. This method is characterized in that the presence of specific enzyme-inhibitor-complexes which form part of the activated blood-coagulation or fibrinolytic system in the bloodplasma to be tested, is ascertained. The method is based on two observed facts, namely: (1) that the enzymes of the blood-coagulation system and of the fibrinolytic system which have generated by activation in a specific step of the coagulation- or fibrinolysis-cascade are neutralized rather rapidly in the bloodplasma by the inhibitors present while forming enzyme-inhibitor-complexes. These complexes can then be isolated from the bloodplasma with physical-chemical agents and are found to be rather stable so that they can be kept for quite some time in their isolated state. (2) Moreover, the new enzyme-inhibitor-complexes found have been found to possess a specific immunogenic structure which deviates from the structure of the precursory molecules such as these occur in bloodplasma. This has made it possible to develop antisera and antibodies against the enzyme-inhibitor-complexes concerned, which antisera and antibodies may then serve as agents in a direct determination of the particular enzyme-inhibitor-complexes in human bloodplasma in an immunochemical way.

The enzyme-inhibitor-complexes which are mentioned by name in U.S. Pat. application Ser. No. 723,187, and of which also the isolation and purification is described, are plasmin-antiplasmin-complex, plasmin-$\alpha_2$-macroglobulin-complex and thrombin-antithrombin III-complex.

Furthermore, the said application describes the preparation of reagents which may be used in the diagnosis-test, namely antisera against the complexes mentioned and suspension of specially prepared red bloodcells or particles of synthetic resin.

The antisera may be prepared in the customary manner with the aid of experimental animals. The fresh antiserum obtained has, however, still to be purified because it comprises not only the specific antibodies against the new immunogenic structures but moreover non-specific antibodies against immunogenic structures present in the precursory molecules or in the starting molecules of the complex. For the purification, two methods are described in U.S. Pat. application Ser. No. 723,187: the first method comprises a chromatography of the fresh antiserum over a column of insolubilized bloodplasma, the filtrate being used further as an antiserum; the second method comprises an incubation with plasminogen and fresh bloodplasma while forming a precipitate, followed up by precipitation of the gamma-globulin-fraction from the remaining fluid and resuspension of this globulin-fraction.

In U.S. Pat. application Ser. No. 723,187 these two methods of purification are applied particularly on the antiserum against plasmin-antiplasmin-complex. Upon application of the antiserum against thrombin-antithrombin III-complex there appears to be a reasonably good purification, but a sufficiently stable antiserum was not obtained. Therefore, upon further research, there has been developed a third method of purification which, when applied to the antiserum against thrombin-antithrombin III-complex, provides a stable antiserum and which, on principle, may be applied to other antisera meant in U.S. Pat. application Ser. No. 723,187.

The invention provides a method of purifying an antiserum against an enzyme-inhibitor-complex which forms part of the activated blood-coagulation or fibrinolytic system in bloodplasma, this method being characterized in that the fresh antiserum is first submitted to immunoprecipitation with fresh human bloodplasma and that the remaining fluid is then submitted to chromatography over an insolubilized enzyme-inhibitor-complex which complex corresponds to the enzyme-inhibitor-complex against which the antiserum was generated. By immunoprecipitation, a good part of the non-specific antibodies may be removed, while by chromatography particularly the specific antibodies are isolated from the mixture, the excess of precursory molecules of the enzyme-inhibitor-complex available in the bloodplasma of the previous step added being removed at the same time.

When applying this two-step method of purification to the antiserum against thrombin-antithrombin III-complex, a purified antiserum is found to be obtained which has a life of more than 1 year and thus comes up to the requirements of stability. When applying to other antisera, as meant in U.S. Pat. application Ser. No. 723,187, similar results may be expected.

When carrying out the method according to the invention, a start is made from fresh antiserum, for instance by injecting rabbits with the particular enzyme-inhibitor complex, regular blood-taking from the rabbits and collecting the serum from the portions of blood taken. In the first step of the purification fresh human blood plasma is added to the fresh antiserum and the mixture is incubated for a short time, due to which a precipitate is obtained which is a reaction-product of various antibodies from the antiserum with antigens from the bloodplasma. The antibodies in this reaction-product are nonspecific for the enzyme-inhibitor-complex used because, in the fresh bloodplasma, there is little or none of such a complex. Incubation and precipitation is done preferably in the presence of a material such as p-nitrophenyl-p-guanidino-benzoate (p-NGB), a quickly acting inhibitor against serin-proteases which prevents activation of the bloodplasma by traces of enzymes in the course of the reaction. After removal of the precipitate the remaining fluid is submitted to the second step.

The second step serves to isolate the specific antibodies, thus obtaining a stable preparation. Should this not be done, there is a chance that in the long run a precipitation is formed again as a consequence of activation of the bloodplasma added and of the formation of an enzyme-inhibitor-complex after the inhibitor against serin-proteases added before has worked out. Therefore, chromatography is applied now, namely over a column of insolubilized enzyme-inhibitor-complex (the same complex which was used for preparing the antiserum). For making the column, the enzyme-inhibitor-complex may be coupled to, for instance, cyanic bromide activated agarose. During chromatography the specific antibodies against the complexes in question are bonded to the column. After washing, they may then be eluted, for instance with a solution of potassium- or ammonium-thiocyanate or of glycin-HCl, after which the eluation, which forms a solution of specific antibodies, is suitable for application as an antiserum in the diagnosis-test.

Further, a special reagent for the diagnosis-test may be prepared from the purified antiserum by contacting it with an aqueous suspension of red bloodcells or a latex of particles of synthetic resin. The reagent thus obtained, in which the specific antibodies of the serum are present on the surface of the bloodcells or particles of synthetic resin, is suitable for carrying out a direct agglutination-test.

Both with the purified antiserum and with the bloodcell- or latex-reagent obtained from it, a diagnosis-test may be carried out according to the methods disclosed in U.S. Pat. application Ser. No. 723,187. In the one case, a sample of bloodplasma to be tested is contacted with the purified antiserum and with a suspension of red bloodcells or a latex of particles of synthetic resin which bear on the surface the particular enzyme-inhibitor-complex (against which the antiserum was prepared, after which it is ascertained whether or not agglutination occurs (agglutination-inhibitor-test). In the other case, the sample of bloodplasma to be tested is contacted with a special bloodcell- or latex-reagent prepared from the purified antiserum, and then it is ascertained whether or not agglutination occurs (direct agglutination-test). In practice various dilutions of the sample of blood to be tested are prepared and it is ascertained at exactly which dilution agglutination does not occur (inhibitor-test) or agglutination does occur (direct test). Thus, in both cases a specific number is obtained which is called the titre. Thanks to the purification of the antiserum, a large difference between the titres in positive and negative outcome may be reached.

Tests with a purified antiserum against thrombin-antithrombin III-complex, respectively with a latex- or bloodcell-reagent prepared from it, have revealed that sometimes the diagnosis-test may give a false positive outcome when the bloodplasma to be tested comprises heparin. Heparin is a polysaccharide which is often administered to patients as an anticoagulation agent since it impedes the modification of fibrogen into fibrin. This heparin acts by formation with complexes with antothrombin III. Probably the false positive outcome in the diagnosis-test is now explained by assuming that the antibodies against thrombin-antithrombin III-complex are also active, at least partially, against heparin-antithrombin III-complex. This false positive outcome can, however, be prevented if the first step of the purification of the T-AT-antiserum, namely the immunoprecipitation with fresh bloodplasma, is made to take place in the presence of heparin. In that case, that portion of the specific antibodies which reacts with both heparin-antithrombin III-complex and the non-specific antibodies from the antiserum, is removed from the antiserum together with the non-specific antibodies, so that later in the diagnosis-test reaction with heparin-containing bloodplasma can not occur. Upon purification in the presence of heparin, only a small portion of the specific antibodies is bonded, so that there remain sufficient specific antibodies to give a reaction with thrombin-anti-thrombin III-complex in the diagnosis-test later on.

Also bloodplasma of a patient with rheumatism-factor in the blood may give a false positive outcome in the diagnosis-test. By treatment of the bloodplasma to be tested with insolubilized human gamma-globulins, this rheumatism-factor can be removed completely from the bloodplasma, after which the remaining plasma is suitable for carrying out the diagnosis-test.

The invention is elucidated more in detail by the following examples.

EXAMPLE I

Purification of antiserum.

In this example an antiserum prepared with thrombin-antithrombin-III-complex is purified by immunoprecipitation with the aid of fresh human bloodplasma, followed up by chromatography over a column of insolubilized thrombin-antithrombin III complex.

Starting materials. An antiserum against thrombin-antithrombin III-complex obtained from rabbits according to example III of U.S. Pat. application Ser. No. 723,187 served as starting material. In the first step fresh human bloodplasma was used, namely blood-bank plasma of normal donors caught on ACD-anticoagulant and further the material para-nitrophenyl-para-guanidinobenzoate (p-NCB of Cyclochemical Comp.). In the chromatography use was made of a column of insolubilized purified T-AT-complex, the preparation of which will be described below. The T-AT-complex needed for this purpose was prepared according to example II of U.S. Pat. application Ser. No. 723,187.

Immunoprecipitation of non-specific antibodies. To 5 ml of antiserum p-NGB to an endconcentration of $10^{-5}$ M and then 2 ml of fresh human bloodplasma were added. After 30 minutes stirring at room temperature the precipitate obtained was removed by separation. The remaining fluid was used for the chromatography.

Preparation of insolubilized thrombin-antithrombin III-complex. 30 ml of agarose (sedimented volume) activated with 3 g of CNBr was mixed with 70 ml of coupling buffer (0,1 M $NaHCO_3$-0,5 M NaCl, pH=9,0) and 20 units O.D. (at 280 nm) of the thrombin-antithrombin III-complex. About 75% of the protein complex was bonded to the agarose. From this product a chromatographying column of 0,9×15 cm was built up.

Chromatography. The remaining fluid of the antiserum was carried over a column of the insolubilized thrombin-antithrombin III-complex prepared as above, at a speed of 10 ml/cm²/hour, which column was equilibrated with a NaCl-phosphate buffer (0,1 M NaCl-0,05 M $Na_2HPO_4$, pH=7,5). The non-adsorbed proteins were washed out carefully with equilibration buffer. Then the bonded antibodies were eluted with 3 M $NH_4SCN$. The eluations collected were dialized against the equilibration buffer and concentrated by vacuum dialysis.

Finally 3,5 ml of purified antiserum (solution of specific antibodies against thrombin-antithrombin III complex) with an O.D. of 1,75 to 280 nm, was obtained. At geldiffusion, this antiserum did not show a clear reaction with fresh heparinfree bloodplasma, but it did show clear precipitinlines with fresh bloodserum. It was suitable as an antiserum for application in an agglutination-inhibiting test.

EXAMPLE II

Purification of antiserum

The method of example I was repeated with the difference that in the immunoprecipitation use was made of fresh human bloodplasma to which heparin was added in advance. This heparin (Liquemine, of Hoffmann-La Roche, a solution with 5000 IU per ml) is used in an amount of 3 IU per ml of bloodplasma. After removal of the precipitate obtained, the remaining fluid was submitted to column-chromatography in the same manner as in example I. Finally 3,5 ml of purified antiserum with an O.D. of 1,75 at 280 nm was obtained. In geldiffusion this solution did not show clear reaction with fresh bloodplasma, but it did show clear precipitin-lines with fresh bloodserum.

EXAMPLE III

Latex-reagent for the diagnosis-test

A special reagent for the performance of the clinical diagnosis-test was prepared by coating particles of synthetic resin on the surface with specific antibodies against T-AT-complex.

A latex of particles of synthetic resin (Bacto-Latex, of Difco Laboratories, Detroit, Mich., USA) was washed twice with a buffer solution (0,02 M glycin, 0.03 M NaCl, pH=9,0) after which the particles were separated off (Sorvall RC2, 10.000 rpm, 5 minutes) and resuspended in the same buffer solution (1,6 time the original volume). Per milliliter of suspension 0,1 ml. of purified antiserum was added, obtained according to example I, and mixed for 60 minutes at room temperature. The coated particles of synthetic resin were separated off, washed with a buffer solution (0,02 M glycin, 0,03 M NaCl, pH=9,0) and resuspended in another buffer solution (0,1 M glycin, 0,15 M NaCl, pH=9,0) to which 1% of cow's albumin (Povite, Amsterdam) and 0,1% of sodiumazide was added. The reagent obtained was suitable for performing a direct agglutination-test.

EXAMPLE IV

Latex-reagent for diagnosis-test

The method of example III was repeated with the difference that on this occasion use was made of an antiserum obtained according to example II. The latex-reagent obtained was suitable for the performance of a direct agglutination-test.

EXAMPLE V

Diagnosis-test with latex-reagent

When performing the diagnosis-test with the reagent of example III, respectively example IV, there were made various solutions of the sample of bloodplasma to be tested in a buffer solution (0,1 M glycin, 0,15 M NaCl, 1% of albumin, pH=9,0). On a little black plate 20 microliter of each of the dilutions or of the buffer solution only was mixed with 20 microliter of the latex-reagent in question. The suspension was mixed continually by sloping the plate to and fro and the agglutination was read after 3 minutes (+ or −) and after 5 minutes (+ or −).

EXAMPLE VI

Outcome of the diagnosis-test

A. Fresh plasma of 40 sound persons agglutinated the latex particles of example III and IV in dilutions of ½ to ⅛, so that the titre was 2–8. To the contrary, a purified T-AT-complex (in a concentration of 10 mg per 100 ml) shew a titre of 160–320. In the serum of fresh blood caught in a glass tube and incubated at room temperature, there arose an agglutinating activity progressive and parallel to the decrease of the prothrombin-concentration which, after 90 minutes, had reached a titre of 320–640.

B. When heparin was added to the fresh bloodplasma, a false positive outcome was obtained with the latex-reagent of example III. The titre, which was 2–8 at the outset, rose proportionally to the heparin-concentration in the bloodplasma and reached a maximum of 160 at a concentration of 2–10 IU of heparin per ml of bloodplasma. At higher heparin-concentrations (10–50 IU per ml) the titre decreased again.

On the other hand, upon repetition of the test with the latex-reagent of example IV (in which the antibodies were pretreated with heparin) no increase of the titre and, therefore, no positive outcome was obtained. In view hereof, for the further tests only the latex-reagent of example IV was used.

C. Fresh bloodplasma of a patient with rheumatism-factor in the serum was found to generate also agglutination of the latex and, therefore, a high titre. However, by treatment of the blood-plasma with insolubilized human gamma-globulins, this agglutinating activity, contrary to the agglutinating activity generated by the coagulation of blood, could be removed.

D. With the aid of the diagnosis-test, the T-AT-titres in 34 plasma samples emanating from hospital patients were determined. The plasma samples which had a titre of more than 8, were tested for rheumatism-factor (RF-latex-test, Behring-Werke) and, if negative, titred out further. One sample was positive for theumatism-factor and was not tested further. 22 samples had a titre of 8 or less, 5 samples had a titre of 12, 6 samples had a titre of 32 or more.

Of the latter 6 samples the titre was compared with the results of the hemostase-test and the diagnosis. Three patients with titres of 32, 64 and 96 suffered of respectively alcoholic liver-cirrhosis, heptoma and acute hepatitis and shew a decrease in the plasma-fibrinogen and an extension of the thrombin-time, each-time suggestive for slow intravascular coagulation. One female patient was examined 24 hours after an abruptio placentae with defibrination, her T-AT-titre was 40. At a check 24 hours later, the titre had already decreased to 4. One female patient with a titre of 32 shew an extensive deep venous thrombosis but without deviations in the hemostase-test. Of one patient with a titre of 64 and a normal hemostase-test, the diagnosis could not be traced.

What I claim is:

1. A method for purifying an antiserum which has been generated against an enzyme-inhibitor-complex, said complex being part of the activated blood-coagulation-or fibrinolytic system in bloodplasma, comprising the steps of:
   (a) immunoprecipitating a freshly generated antiserum with fresh human bloodplasma and thereby forming a precipitate and a remaining fluid; and
   (b) subjecting the said remaining fluid to chromatographic separation over an insolubilized enzyme-inhibitor-complex, said complex corresponding to the enzyme-inhibitor-complex against which the antiserum has been generated, in order to separate a purified antiserum from said remaining fluid.

2. A method as recited in claim 1, wherein an antiserum against thrombin-antithrombin III-complex is purified by immunoprecipitating the fresh antiserum with fresh human bloodplasma and by subjecting the remaining fluid to chromatographic separation over insolubilized thrombin-antithrombin III-complex.

3. A method according to claim 1, wherein the said immunoprecipitation takes place in the presence of an inhibitor against serin-protease.

4. A method according to claim 1 for the purification of an antiserum against thrombin-antithrombin III-complex, wherein heparin is added to said bloodplasma so that immunoprecipitation takes place in the presence of heparin.

5. A method according to claim 1, wherein the insolubilized enzyme-inhibitor-complex is obtained by bonding the enzyme-inhibitor complex used to prepare the antiserum to cyanic bromide-activated agarose.

6. A method according to claim 1 wherein in said chromatographic separation the antiserum is adsorbed upon said insolubilized enzyme-inhibitor-complex and a solution of potassium- or ammoniumthiocyanate or of glycin-HCl is used to elute purified antiserum from said insolubilized enzyme-inhibitor-complex.

7. An antiserum against an enzyme-inhibitor-complex purified by a method of claim 1.

8. A method of preparing a special reagent for an immunochemical method of determination wherein an aqueous suspension of red bloodcells or a latex of particles of synthetic resin is contacted with an antiserum as obtained in claim 1 and thereby obtaining said suspension of red bloodcells or said latex with antibodies from the antiserum present on the surface thereof.

9. A special reagent for a method of immunochemical determination obtained by the method of claim 8.

10. A method of determining an activation of the blood-coagulation- and/or fibrinolytic system in bloodplasma comprising the steps of: contacting the bloodplasma to be examined with an antiserum obtained as in claim 1 and with a suspension of red bloodcells or a latex of particles of synthetic resin which bear the enzyme-inhibitor-complex used to prepare the antiserum on the surface thereof; and subsequently ascertaining whether or not agglutination occurs.

11. A method of determining an activation of the blood-coagulation system and/or fibrinolytic system in bloodplasma by contacting the bloodplasma to be examined with a special reagent comprising a latex of particles of synthetic resin or a suspension of red bloodcells having antibodies from said antiserum on the surface of said particles or red blood cells, said special reagent having been prepared by the method of claim 8; and by subsequently ascertaining whether or not agglutination occurs.

12. A method of preparing a special reagent for an immunochemical method of determination wherein an aqueous suspension of red bloodcells or a latex of particles of synthetic resin is contacted with an antiserum as obtained in claim 4 and thereby obtaining said suspension of red bloodcells or said latex with antibodies from the antiserum present on the surface thereof.

13. A method of determining an activation of the blood-coagulation and/or fibrinolytic system in bloodplasma comprising the steps of: contacting the bloodplasma to be examined with an antiserum obtained as in claim 4 and with a suspension of red bloodcells or a latex of particles of synthetic resin which bear the enzyme-inhibitor-complex used to prepare the antiserum on the surface thereof; and subsequently ascertaining whether or not agglutination occurs.

14. A method of determining an activation of the blood-coagulation system and/or fibrinolytic system in bloodplasma by contacting the bloodplasma to be examined with a special reagent comprising a latex of particles of synthetic resin or a suspension of red bloodcells having antibodies from said antiserum on the surface of said particles or red bloodcells, said special reagent having been prepared by the method of claim 12; and by subsequently ascertaining whether or not agglutination occurs.

* * * * *